US011235098B2

(12) United States Patent
Fontecchio

(10) Patent No.: US 11,235,098 B2
(45) Date of Patent: Feb. 1, 2022

(54) INSULIN PEN HOLDER AND STORAGE DEVICE

(71) Applicant: Anthony Michael Fontecchio, Canon City, CO (US)

(72) Inventor: Anthony Michael Fontecchio, Canon City, CO (US)

( * ) Notice: Subject to any disclaimer, the term of this patent is extended or adjusted under 35 U.S.C. 154(b) by 434 days.

(21) Appl. No.: 15/651,812

(22) Filed: Jul. 17, 2017

(65) Prior Publication Data

US 2018/0140767 A1 May 24, 2018

Related U.S. Application Data

(60) Provisional application No. 62/343,067, filed on May 30, 2016.

(51) Int. Cl.
*A61M 5/00* (2006.01)
*A61J 1/16* (2006.01)
*B65D 25/22* (2006.01)

(52) U.S. Cl.
CPC .............. *A61M 5/002* (2013.01); *A61J 1/16* (2013.01); *B65D 25/22* (2013.01)

(58) Field of Classification Search
CPC ................................. B65D 25/22; A61J 1/16
USPC ........ 206/443, 481, 480; 211/72, 69.9, 69.1, 211/74
See application file for complete search history.

(56) References Cited

U.S. PATENT DOCUMENTS

| 230,772 | A | * | 8/1880 | Hafely | B65D 85/24 206/380 |
| 822,984 | A | * | 6/1906 | Richter | A47B 73/00 206/446 |
| 1,459,787 | A | * | 6/1923 | McGee | A47G 25/12 211/63 |
| 1,562,114 | A | * | 11/1925 | Micheli | F42B 39/30 206/3 |
| 2,054,355 | A | * | 9/1936 | Anderson, Jr. | B65D 5/504 206/315.2 |
| 2,593,042 | A | * | 4/1952 | Lynskey | A63B 57/203 211/70.1 |
| 2,598,492 | A | * | 5/1952 | Boes | B65D 25/105 206/480 |
| 2,903,139 | A | * | 9/1959 | Penman | G09F 5/042 206/725 |
| 2,959,296 | A | * | 11/1960 | Case | B43K 23/001 211/69.1 |
| 3,199,669 | A | * | 8/1965 | Straus | B01L 9/06 206/763 |
| 3,707,227 | A | * | 12/1972 | Britt | B01L 9/06 206/443 |
| 3,813,813 | A | * | 6/1974 | Powell | A01G 9/02 47/68 |
| 4,044,757 | A | * | 8/1977 | McWhorter | A61M 3/0262 600/432 |

(Continued)

*Primary Examiner* — J. Gregory Pickett
(74) *Attorney, Agent, or Firm* — Robert N. Rountree

(57) ABSTRACT

An injector pen or medication vial holder and storage device is disclosed. The device includes a base plate having first and second opposing sides. An attachment structure is affixed to the first side of the base plate. Plural retaining members are connected to the second side of the base plate. Each retaining member is configured to receive a respective injector pen. A support member is connected to the base plate and arranged to support one end of each said respective injector pen.

17 Claims, 5 Drawing Sheets

(56) References Cited

U.S. PATENT DOCUMENTS

| | | | | |
|---|---|---|---|---|
| 4,236,338 | A * | 12/1980 | Musgrave | F41C 27/00 42/90 |
| 4,489,830 | A * | 12/1984 | Charlebois | G02B 6/3801 206/443 |
| 4,572,371 | A * | 2/1986 | Asenbauer | B01L 9/06 206/443 |
| 4,778,053 | A * | 10/1988 | Hakansson | B65D 75/42 206/217 |
| 4,929,427 | A * | 5/1990 | Guala | G01N 15/05 206/366 |
| 4,961,505 | A * | 10/1990 | Moeller | A47F 7/0035 211/65 |
| 5,080,240 | A * | 1/1992 | Williams | B25H 3/04 211/13.1 |
| 5,115,816 | A * | 5/1992 | Lee | A61M 5/1782 600/562 |
| 5,226,895 | A * | 7/1993 | Harris | A61J 1/1406 604/208 |
| 5,484,066 | A * | 1/1996 | Luisi | B43K 23/002 211/69.8 |
| 5,700,429 | A * | 12/1997 | Buhler | B01L 9/06 422/560 |
| 5,806,692 | A * | 9/1998 | Pepper | A47B 96/027 211/126.16 |
| 6,123,205 | A * | 9/2000 | Dumitrescu | B01L 9/06 206/443 |
| 6,206,212 | B1 * | 3/2001 | Loew | A47F 5/04 211/162 |
| 6,401,943 | B1 * | 6/2002 | Root | A47K 1/09 206/362.1 |
| 6,955,259 | B1 * | 10/2005 | Jesse | A61M 5/008 206/366 |
| 7,059,077 | B2 | 6/2006 | Tai et al. | |
| 7,721,899 | B2 * | 5/2010 | Lambert | A47K 1/09 211/119.009 |
| 7,954,639 | B2 * | 6/2011 | Carney | A47B 43/003 206/579 |
| 8,955,697 | B2 * | 2/2015 | Spilotro | A47B 81/00 211/60.1 |
| 9,084,593 | B2 * | 7/2015 | Yakel | A61B 19/0271 |
| 9,383,179 | B1 * | 7/2016 | Spilotro | F42B 39/28 |
| 2003/0042218 | A1 * | 3/2003 | Bell | B43M 99/00 211/88.01 |
| 2003/0047474 | A1 * | 3/2003 | Dahlson | B65D 5/4204 206/423 |
| 2006/0054575 | A1 * | 3/2006 | Robertson | A47F 3/0486 211/75 |
| 2006/0243622 | A1 * | 11/2006 | Lyman, Jr. | B43M 99/006 206/443 |
| 2008/0255520 | A1 * | 10/2008 | Henderson | A61M 5/19 604/191 |
| 2008/0272078 | A1 * | 11/2008 | Belokin | A47F 5/08 211/126.1 |
| 2010/0300994 | A1 * | 12/2010 | Turner-Wiltshire | A47K 10/10 211/16 |
| 2011/0139732 | A1 * | 6/2011 | Caban | A47G 29/087 211/13.1 |
| 2012/0234783 | A1 * | 9/2012 | Schneider | A47F 5/0043 211/133.6 |
| 2014/0076756 | A1 * | 3/2014 | Sweetman | A01K 1/011 206/349 |

* cited by examiner

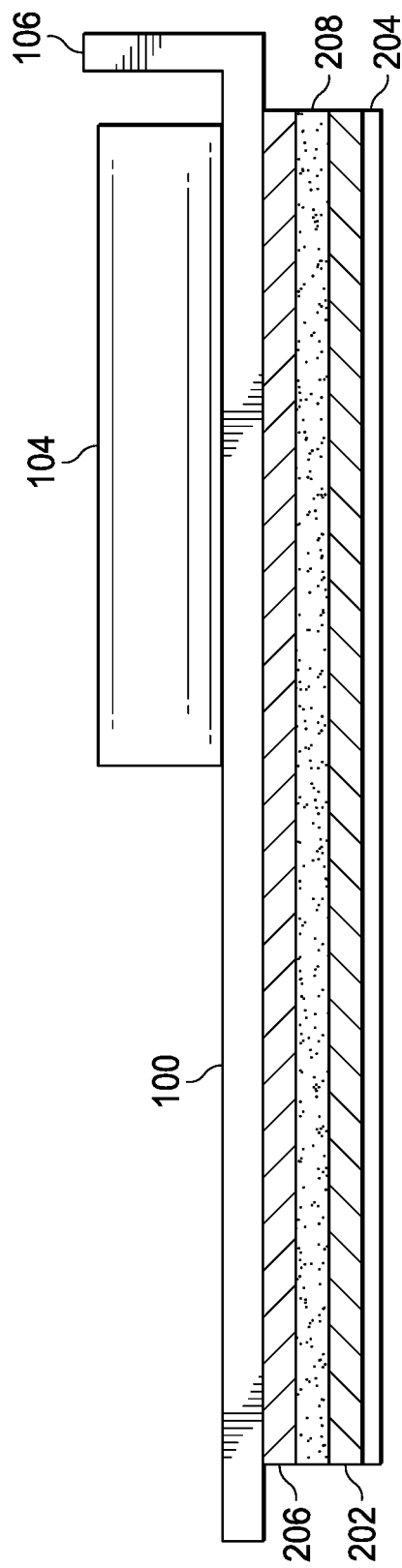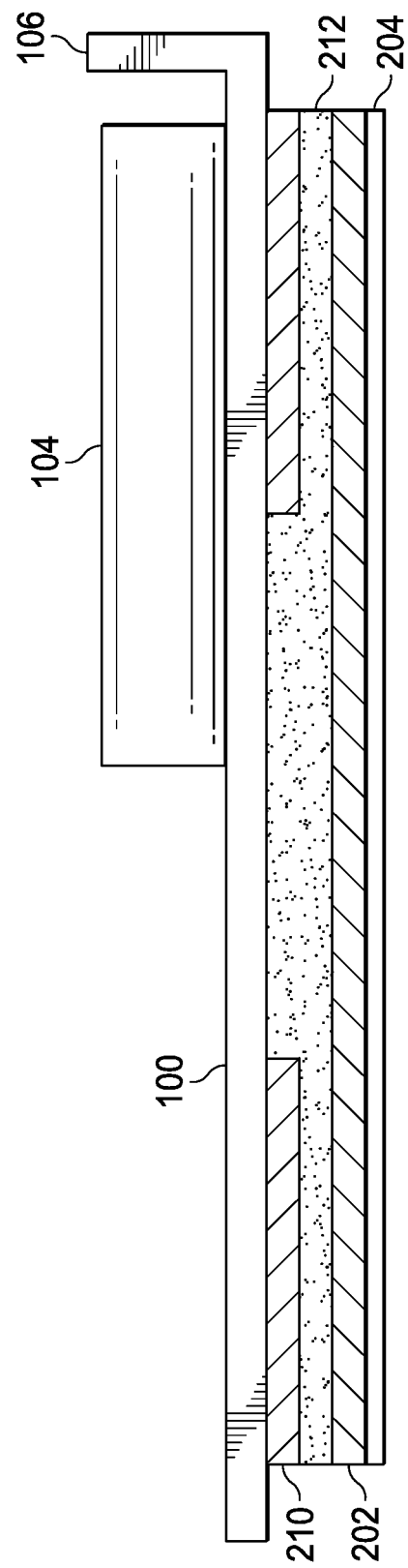

INSULIN PEN HOLDER AND STORAGE DEVICE

CROSS REFERENCE TO RELATED APPLICATION

This application claims the benefit of priority under 35 U.S.C. § 119(e) to U.S. Provisional Application Ser. No. 62/343,067, filed May 30, 2016, which is incorporated herein by reference in its entirety.

BACKGROUND OF THE INVENTION

According to a 2014 study by the Center for Disease Control (CDC) there are approximately 29.1 million diagnosed and undiagnosed diabetics in this country. This is approximately 9.3% of the population of the United States. Approximately 8.1 million of the 29.1 million or 27.8% are undiagnosed. In general, diabetes is a disease that affects a body's ability to produce insulin, a protein that the body produces to assist in the use of glucose. Diabetes, therefore, often produces an abnormally high level of blood sugar in the body. The most common forms of diabetes are Type 1 and Type 2 diabetes. Type 1 is less common and means the body does not produce insulin. It affects approximately 5% of the diabetic population. Type 2 is more common and means the body either does not produce enough insulin or is unable to use insulin properly. It affects approximately 95% of the diabetic population. There are also other less common forms of diabetes such as gestational diabetes, which may affect pregnancies.

Both Type 1 and Type 2 diabetes are typically treated with insulin injections as prescribed by a doctor. Depending on the severity of diabetes with the individual patient, the doctor may prescribe daily injections of insulin so the patient maintains a normal lifestyle. Separation from these periodic insulin injections may result in serious illness or even death. These periodic insulin injections may require the patient to maintain a vial of insulin and a quantity of syringes in order to administer the injections as required. Insulin, however, must be refrigerated prior to use to maintain an acceptable shelf life. This means the patient cannot expose the vial of insulin to room temperature environments for extended periods. Consequently, the patient's freedom is effectively limited by a need to remain near a source of refrigerated insulin.

Insulin injector pens were developed to reduce a patient's need to remain near a refrigerated vial of insulin. There are several manufacturers of these pens such as AstraZeneca, Lilly, Novo Nordisk, and others. Each pen includes a needle, a small vial with a single prescribed dose of insulin, and a protective enclosure. These patient-specific pens are relatively expensive but provide added freedom to the patient. For example, the patient may carry one or two pens away from a refrigerated environment for a brief time without degrading an entire vial of insulin. The pens also provide a more convenient means of injection, since they already contain a prescribed dose of insulin. Since they are patient-specific, however, there is an inherent delay between prescription order placement and arrival of the pens. Thus, the patient must always keep track of the remaining number of pens in order to timely refill an individual prescription.

These patient-specific insulin pens must be stored in a refrigerated environment prior to use to maintain their shelf life. This is typically the patient's home refrigerator. In some cases the patient may store the pens in a box in the refrigerator where they occupy shelf space and may be exposed to food or liquid spills. The pens may be stored in a butter compartment of the refrigerator door. This not only occupies the butter compartment, but agitation from door opening and closing may create bubbles within the insulin dose of the pen. The pens may also be stored in other places in the refrigerator. These storage spaces, however, occupy refrigerator space intended for food storage and present several other problems. Individual pens may be misplaced or hidden by food packages. The pens are subject to contamination by food. The patient may not be aware of a remaining number of pens, which may be stored in different areas of the refrigerator.

In view of the foregoing problems, embodiments of the present invention are directed to more efficient storage of insulin injector pens within a refrigerated environment.

BRIEF SUMMARY OF THE INVENTION

In a first embodiment of the present invention, an injector pen holder is disclosed. The injector pen holder includes a base plate having first and second opposing sides. An attachment structure is affixed to the first side. Plural retaining members are connected to the second side. Each retaining member is configured to receive a respective injector pen. A support member is connected to the base plate and arranged to support one end of each respective injector pen.

In a second embodiment of the present invention, an injector pen holder is disclosed. The injector pen holder includes a base plate. Plural retaining members are connected to a side of the base plate. Each retaining member is configured to receive a respective injector pen. A support member is connected to the base plate and arranged to support one end of each respective injector pen.

In a third embodiment of the present invention, an injector pen holder is disclosed. The injection pen holder includes a base plate. Plural retaining members are connected to a side of the base plate. Each retaining member is configured to receive a respective injector pen. A support member is connected to the base plate and arranged to support the base plate.

BRIEF DESCRIPTION OF THE SEVERAL VIEWS OF THE DRAWING

FIGS. 2A through 2D are side views of the injector pen holder and storage device showing various attachment structures;

DETAILED DESCRIPTION OF THE INVENTION

Figure 1:
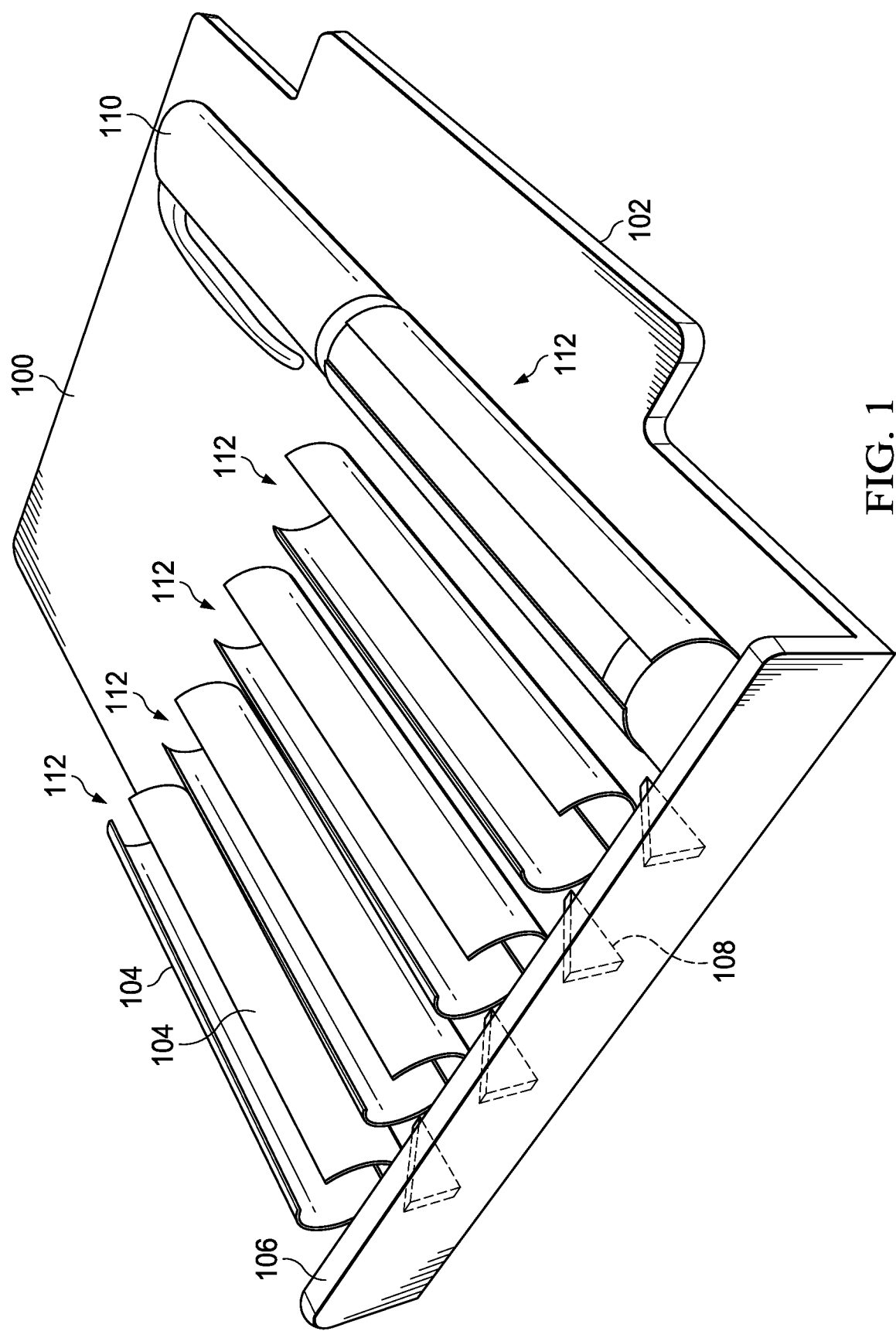
FIG. 1 is a structural diagram of an injector pen in an injector pen holder and storage device according to an embodiment of the present invention.

Embodiments of the present invention provide significant advantages over injector pen storage methods of the prior art as will become evident from the following detailed description. In the following detailed description, the same reference numerals in the various drawing figures refer to substantially the same elements.

Referring to FIG. 1, there is a structural diagram of an injector pen 110 in an injector pen holder and storage device according to an embodiment of the present invention. The injector pen 110 includes a needle, a small vial with a single prescribed dose of insulin or other medication, and a protective enclosure. The injector pen holder includes a planar base plate 100 having first and second opposing sides. The base plate 100 may be a single layer or plural separate layers. A tab 102 may display manufacturer or prescription information. A plurality of retaining members 112 are formed by pairs of sides 104 and connected to the second side of the base plate. The sides 104 are preferably flexible and may be formed in a semicircular configuration as shown. Each respective pair of opposing sides extends from the second side of the base plate toward a respective opposing side to a respective first edge parallel to a first edge of the respective opposing side and to the second side of the base plate forming a region there between. Each pair of sides 104 may be formed of injection molded plastic together with the base plate 100. Alternatively, the sides 104 may be attached to the base plate 100 by hinge means and may incorporate springs to apply retention pressure to the sides of an injector pen 110.

Still referring to FIG. 1, a support member 106 is connected and parallel to an edge of the base plate 100 and arranged to contact and support one end of injector pen 110. Triangular gusset members 108 may be included to add structural rigidity between base plate 100 and support member 106. The support member 106 may be formed of plastic by injection molding in a single unit together with base plate 100, sides 104, and gusset members 108. The support member 106 is arranged to contact and support one end of injector pen 110 in a respective retaining member 112. In one embodiment, support member 106 may have sufficient width to support base plate 100 with respective injector pens in each retaining member 112 in a vertical orientation on a horizontal surface such as a shelf of a refrigerator. In another embodiment, the pen holder and storage device may be suspended by base plate 100 from a refrigerator shelf. In yet another embodiment, support member 106 is configured to constrain movement of injector pen 110 when mounted to a side wall of a refrigerator in a vertical, horizontal, or other arbitrary orientation. In this embodiment, an attachment structure is affixed to a reverse side of the base plate to facilitate mounting of the injector pen holder and storage device as will be discussed in detail.

Figure 2A:
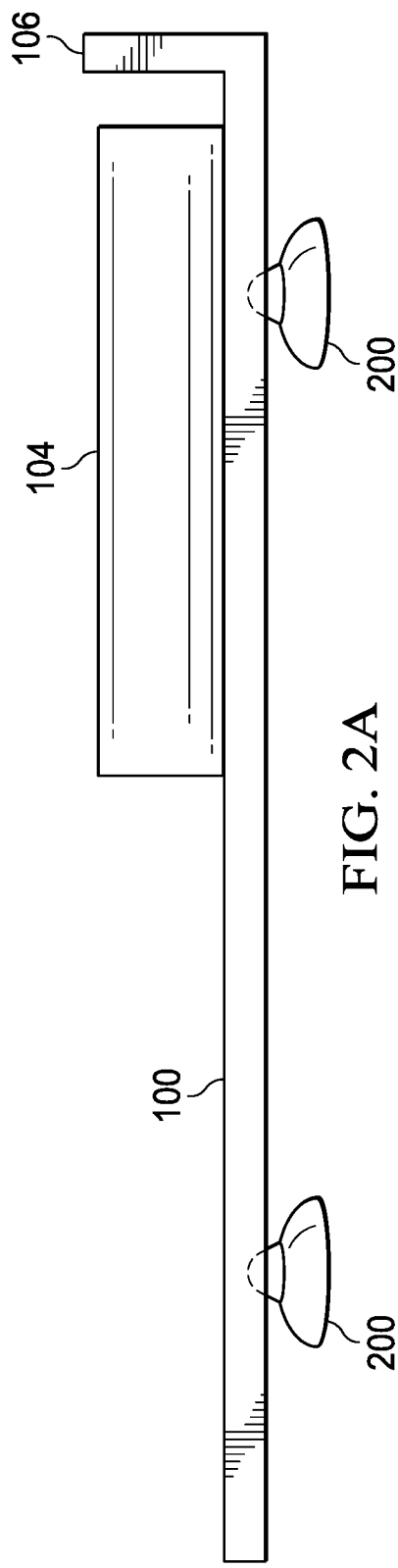

Referring now to FIGS. 2A through 2D there are several attachment structures that may be used to attach the injector pen holder and storage device to a vertical wall such as a side wall of a refrigerator. FIG. 2A is a side view of the injector pen holder and storage device showing a first embodiment of the attachment structure. Rubber or soft plastic suction cups 200 are affixed to the reverse side of base plate 100 and arranged to mount the injector pen holder and storage device to a smooth inner side wall of the refrigerator.

Figure 2B:
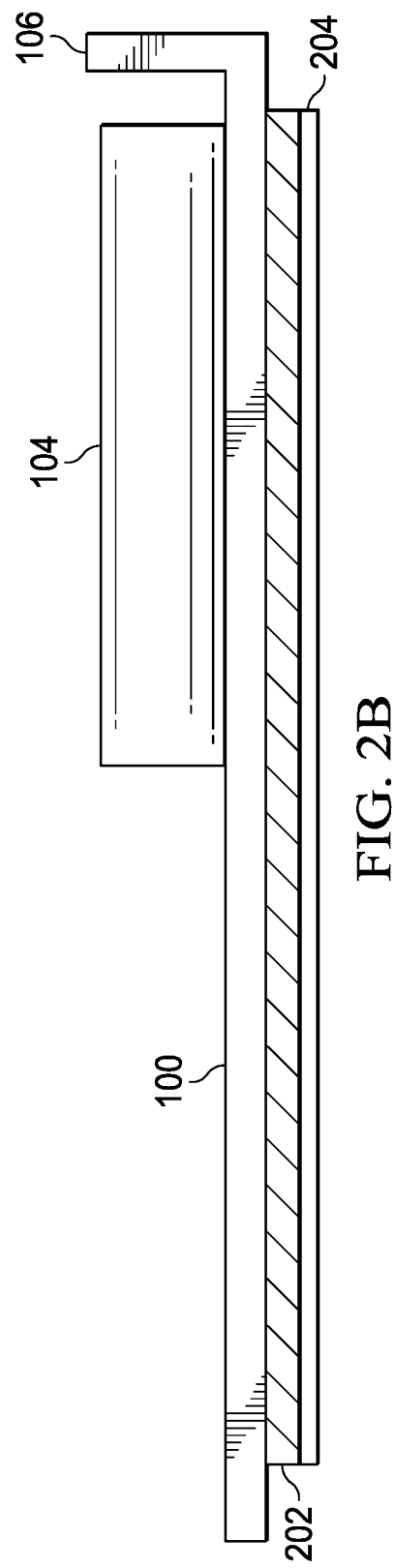

FIG. 2B is a side view showing a second embodiment of the attachment structure. Adhesive layer 202 is affixed to the reverse side of base plate 100. This adhesive layer 202 may be double sided tape such as produced by the 3M® Company. A protective layer 204 is formed over adhesive layer 202 and removed prior to mounting the pen holder and storage device to a smooth inner wall of the refrigerator.

FIG. 2C is a side view showing a third embodiment of the attachment structure. A first layer 206 of a hook and loop material such as Velcro® is adhesively affixed to the reverse side of base plate 100. A complementary second layer 208 of the hook and loop material such as Velcro® is attached by contact to the first layer. Adhesive layer 202 is affixed to the second layer opposite the first layer, and a protective layer 204 is formed over adhesive layer 202. Protective layer 204 is removed prior to mounting the pen holder and storage device to a smooth inner wall of the refrigerator.

FIG. 2D is a side view showing a fourth embodiment of the attachment structure. A first bracket fixture 210 is adhesively affixed or otherwise connected to the reverse side of base plate 100. Alternatively, the first bracket fixture 210 may be formed by plastic injection molding together with base plate 100 and other components of the pen holder and storage device. A second and complementary bracket fixture 212 is structurally engaged with the first bracket fixture. Adhesive layer 202 is affixed to the second bracket fixture 212 opposite the first bracket fixture 210. A protective layer 204 is formed over adhesive layer 202 and removed prior to mounting the pen holder and storage device to a smooth inner wall of the refrigerator.

There are several significant advantages of the foregoing embodiments of the present invention. First, injector pens are always stored in the same place in their own respective retaining members so that they will not be misplaced. Second, the number of available insulin pens is always visible as mounted on an inner side wall or horizontal shelf of a refrigerator. Third, retaining members of the pen holder and storage device are open and readily accessible for easy cleaning. Moreover, the pen holder and storage device may be readily removed for cleaning or replacement. Fourth, smooth inner sidewalls and horizontal shelves of the refrigerator are relatively stable and will not agitate stored insulin pens, thereby forming bubbles in the insulin. Finally, the retaining members with flexible sides will accommodate numerous insulin injector pens from various manufacturers.

Figure 3:
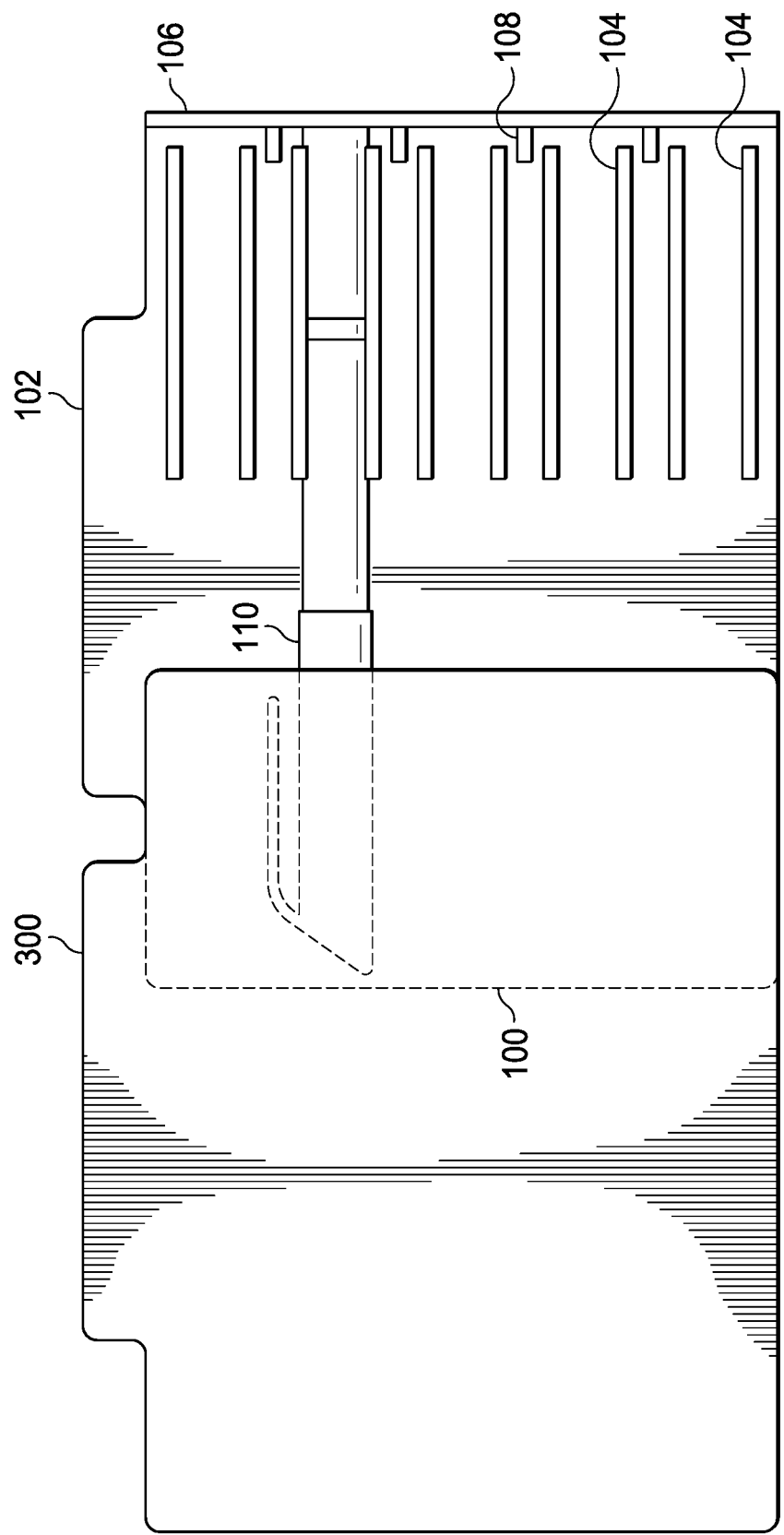
FIG. 3 is a top view of the injector pen holder and storage device with an optional cover.

Turning now to FIG. 3, there is a top view of the injector pen holder and storage device with an optional cover 300. The cover 300 may operate in a horizontal, vertical, or arbitrary orientation for virtually any mounting arrangement of the pen holder and storage device. The cover 300 may include a locking means to structurally engage with the base plate 100 and support member 106. Additionally, the cover may be formed from multiple pieces that open in opposing directions. The cover 300 may be particularly useful when multiple pen holder and storage devices are attached to an inner wall of a refrigerator. Thus, storage devices that are full of injector pens may remain covered, and only pen holders that are currently in use may remain uncovered.

Figure 4:
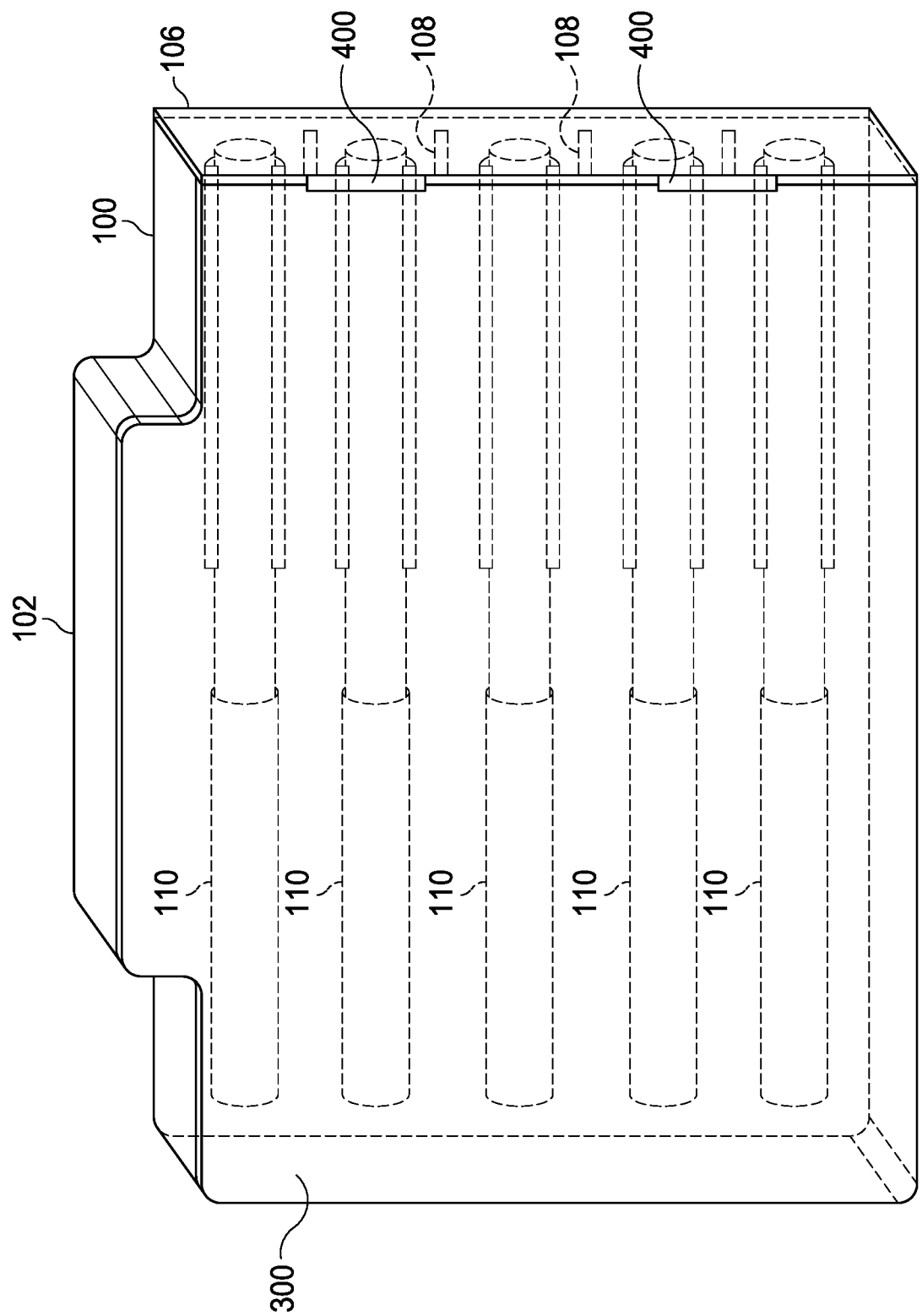
FIG. 4 is a structural diagram of the injector pen holder and storage device with several injector pens and an optional hinged cover.

FIG. 4, is a structural diagram of the injector pen holder and storage device with several injector pens 110 and an optional hinged cover 300. In this embodiment optional cover 300 is attached by hinge means 400 so support member 106. The cover 300 may operate in a horizontal, vertical, or arbitrary orientation for virtually any mounting arrangement of the pen holder and storage device. The cover 300 may include a locking means to structurally engage with the base plate 100 or support member 106. Additionally, the cover may be formed from multiple pieces that open in opposing directions. As with the embodiment of FIG. 3, the cover 300 may be particularly useful when multiple pen holder and storage devices are attached to an inner wall of a refrigerator. Thus, storage devices that are full of injector pens may remain covered, and only pen holders that are currently in use remain uncovered.

Still further, while numerous examples have thus been provided, one skilled in the art should recognize that various modifications, substitutions, or alterations may be made to the described embodiments while still falling within the inventive scope as defined by the following claims. For example, the injector pen or medication vial holder and storage device is readily adaptable for storing different types of injector pens. For example, the injector pen or medication vial holder and storage device may store injector pens or medication vials with allergy medication, weight loss medication, or other medication. Moreover, the pen or vial holder and storage device is readily adaptable to other surfaces in non-refrigerated environments where refrigeration of the medication is not necessary. Other combinations will be readily apparent to one of ordinary skill in the art having access to the instant specification.

The invention claimed is:

1. An injector pen holder, comprising:
a base plate having first and second opposing sides;
an attachment structure affixed to the first side of the base plate;
a plurality of retaining members connected to the second side of the base plate, each retaining member having a respective pair of opposing sides, wherein each opposing side extends from the second side of the base plate toward a respective opposing side to a respective first edge parallel to a first edge of the respective opposing side and to the second side of the base plate forming a region there between configured to receive a respective injector pen; and
a support member comprising a planar surface perpendicular to the base plate, the support member connected and parallel to an edge of the base plate, and the support member arranged to contact and support one end of each said respective injector pen.

2. The injector pen holder of claim 1, comprising a gusset member connected between the base plate and the support member.

3. The injector pen holder of claim 1, wherein the injector pen holder is an insulin injector pen holder.

4. The injector pen holder of claim 1, wherein the attachment structure comprises a plurality of suction cups.

5. The injector pen holder of claim 1, wherein the attachment structure comprises:
an adhesive layer affixed to the first side of the base plate; and
a protective film affixed to the adhesive layer opposite the first side.

6. The injector pen holder of claim 1, wherein the attachment structure comprises:
a first layer affixed to the first side of the base plate;
a second layer in contact with the first layer and configured to adhere to the first layer on contact;
an adhesive layer affixed to the second layer opposite first layer; and
a protective film affixed to the adhesive layer opposite the second layer.

7. The injector pen holder of claim 1, wherein the attachment structure comprises:
a first bracket fixture affixed to the first side of the base plate;
a second bracket fixture in contact with the first bracket fixture and configured to structurally engage the first bracket fixture;
an adhesive layer affixed to the second bracket fixture opposite first bracket fixture; and
a protective film affixed to the adhesive layer opposite the second bracket fixture.

8. The injector pen holder of claim 1, wherein the base plate, the plurality of retaining members, and the support member are formed from a single piece of injection molded plastic.

9. An injector pen holder, comprising:
a base plate of the injector pen holder having first and second opposing sides;
a plurality of retaining members connected to the second side of the base plate, each retaining member having a respective pair of opposing sides, wherein each opposing side extends from the second side of the base plate toward a respective opposing side to a respective first edge parallel to a first edge of the respective opposing side and to the second side of the base plate forming a region there between configured to receive a respective injector pen; and
a support member comprising a planar surface perpendicular to the base plate, the support member connected and parallel to an edge of the base plate, and the support member arranged to contact and support one end of each said respective injector pen.

10. The injector pen holder of claim 9, wherein the injector pen holder is an insulin injector pen holder.

11. The injector pen holder of claim 9, comprising:
an adhesive layer affixed to the first side of the base plate; and
a protective film affixed to the adhesive layer opposite the first side.

12. The injector pen holder of claim 9, comprising:
a first layer affixed to the first side of the base plate;
a second layer in contact with the first layer and configured to adhere to the first layer on contact;
an adhesive layer affixed to the second layer opposite first layer; and
a protective film affixed to the adhesive layer opposite the second layer.

13. The injector pen holder of claim 9, wherein each of the plurality of retaining members comprises a pair of flexible sides configured to retain an injector pen.

14. A medication vial holder, comprising:
a base plate of the medication vial holder having first and second opposing sides;
a plurality of retaining members connected to the second side of the base plate, each retaining member having a respective pair of opposing sides, wherein each opposing side extends from the second side of the base plate toward a respective opposing side to a respective first edge parallel to a first edge of the respective opposing side and to the second side of the base plate forming a region there between configured to receive a respective medication vial; and
a support member comprising a planar surface perpendicular to the base plate, the support member connected and parallel to an edge of the base plate, and the support member arranged to contact and support one end of each said respective medication vial pen.

15. The medication vial holder of claim 14, wherein the medication vial holder comprises an insulin vial holder.

16. The medication vial holder of claim 14, comprising:
an adhesive layer affixed to the first side of the base plate; and
a protective film affixed to the adhesive layer opposite the first side.

17. The medication vial holder of claim 14, comprising:
a first layer affixed to the first side of the base plate;
a second layer in contact with the first layer and configured to adhere to the first layer on contact;
an adhesive layer affixed to the second layer opposite first layer; and
a protective film affixed to the adhesive layer opposite the second layer.

* * * * *

UNITED STATES PATENT AND TRADEMARK OFFICE
CERTIFICATE OF CORRECTION

PATENT NO. : 11,235,098 B2
APPLICATION NO. : 15/651812
DATED : February 1, 2022
INVENTOR(S) : Anthony Michael Fontecchio Page 1 of 1

It is certified that error appears in the above-identified patent and that said Letters Patent is hereby corrected as shown below:

In the Claims

Column 6, approximate Line 52, In Claim 14, last line, delete "pen".

Signed and Sealed this
Twelfth Day of April, 2022

Drew Hirshfeld
*Performing the Functions and Duties of the
Under Secretary of Commerce for Intellectual Property and
Director of the United States Patent and Trademark Office*